(12) United States Patent
Cowden

(10) Patent No.: US 6,673,939 B2
(45) Date of Patent: Jan. 6, 2004

(54) PROCESS FOR THE PREPARATION OF 1,2,4-TRIAZOLIN-5-ONE DERIVATIVES

(75) Inventor: Cameron John Cowden, Stanstead Abbotts (AU)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/311,389

(22) PCT Filed: Jun. 13, 2001

(86) PCT No.: PCT/GB01/02617

§ 371 (c)(1),
(2), (4) Date: Feb. 5, 2003

(87) PCT Pub. No.: WO01/96315

PCT Pub. Date: Dec. 20, 2001

(65) Prior Publication Data

US 2003/0187274 A1 Oct. 2, 2003

(51) Int. Cl.⁷ .................................... C07D 249/12
(52) U.S. Cl. .................................... 548/263.2; 544/132
(58) Field of Search ..................... 548/263.2

(56) References Cited

FOREIGN PATENT DOCUMENTS

| WO | WO 99 18089 A | 4/1999 |
| WO | WO 99 65900 A | 12/1999 |

OTHER PUBLICATIONS

C.J. Cowden: *Tetrahedron Letters*, No. 41, Oct. 28, 2000 pp. 8661–8664.

K. Kamata et al; *Heterocycles.*, vol. 51, No. 2, Feb. 1, 1999, pp. 373–378.

*Primary Examiner*—Robert W. Ramsuer
(74) *Attorney, Agent, or Firm*—J. Eric Thies; Melvin Winokur

(57) ABSTRACT

The present invention relates to a process for the preparation of a compound of formula (I) wherein R represents hydrogen, $C_{1-10}$alkyl, halo$C_{1-10}$alkyl or aryl; which are useful intermediates in the preparation of morpholine derivatives of formula (A). Compounds of formula (A) are useful as therapeutic agents.

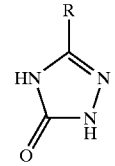

(I)

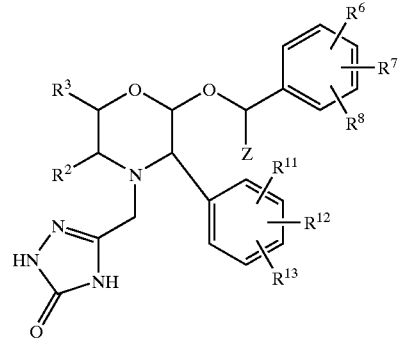

(A)

10 Claims, No Drawings

PROCESS FOR THE PREPARATION OF 1,2,4-TRIAZOLIN-5-ONE DERIVATIVES

CROSS REFERENCE TO RELATED APPLICATIONS

This application is a U.S. National Phase application under 35 U.S.C. § 371 of PCT Application No. PCT/GB01/02617, filed Jun. 13, 2001, which claims priority under 35 U.S.C. § 119 from GB Application No. 0014876.7, filed Jun. 16, 2000.

The present invention relates to a process for the preparation of 1,2,4-triazolin-5-one derivatives which are useful as intermediates in the synthesis of therapeutic agents. In particular, the present invention relates to the preparation of the compound 3-chloromethyl-1,2,4triazolin-5-one.

Compounds of formula (A), below, which are described in International patent specification No. WO 95/16679 (published Jun. 22, 1995), are potent and selective substance P (or neurokinin-1) receptor antagonists.

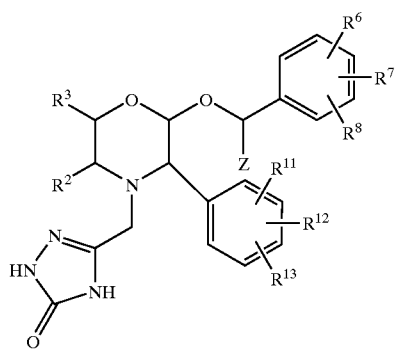

(A)

wherein
R$^2$ and R$^3$ are independently selected from the group consisting of:
(1) hydrogen,
(2) C$_{1-6}$alkyl,
(3) C$_{2-6}$alkenyl, and
(4) phenyl;
R$^6$, R$^7$ and R$^8$ are independently selected from the group consisting of:
(1) hydrogen,
(2) C$_{1-6}$alkyl,
(3) fluoro,
(4) chloro,
(5) bromo,
(6) iodo, and
(7) —CF$_3$;
R$^{11}$, R$^{12}$ and R$^{13}$ are independently selected from the group consisting of:
(1) hydrogen,
(2) C$_{1-6}$alkyl,
(3) fluoro,
(4) chloro,
(5) bromo,
(6) iodo, and
(7) —CF$_3$; and
Z is C$_{1-4}$alkyl.

In particular, the compound 2-(R)(1(R)-(3,5-bis(trifluoromethyl)phenyl)ethoxy)-3-(s)-(4-fluorophenyl)4(3-(5-oxo-1H,4H-1,2,4-triazolo)methyl)morpholine is a potent, long-lasting, nonpeptide substance P antagonist based upon its ability to displace [$^{125}$I]substance P from human NK$_1$ receptors (see Hale et al., *J. Med. Chem.* (1998) 41, 4607). This compound is, therefore, a potential therapeutic candidate for a range of afflictions including chemotherapy-induced emesis, depression and anxiety.

International patent specification No. WO 95/16679 describes the preparation of 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine (hereinafter referred to as Compound A), which has the structure:

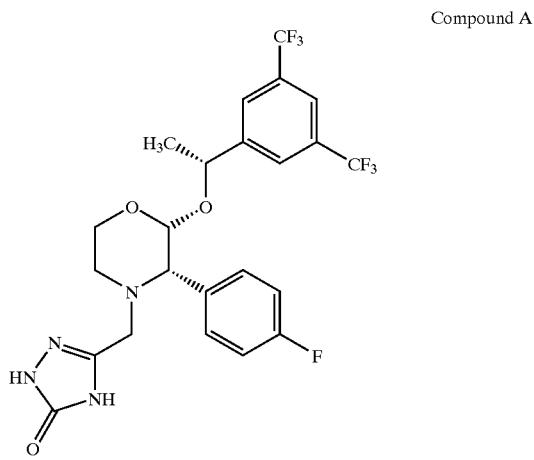

Compound A by a two-step process starting from 2-(R)-(1-(R)-(3,5-bis(trifluoromethyl)-phenyl)ethoxy)3-(S)-(4-fluorophenyl)morpholine. With reference to Examples 70 and 75 in WO 95/16679, Compound A is prepared as follows:

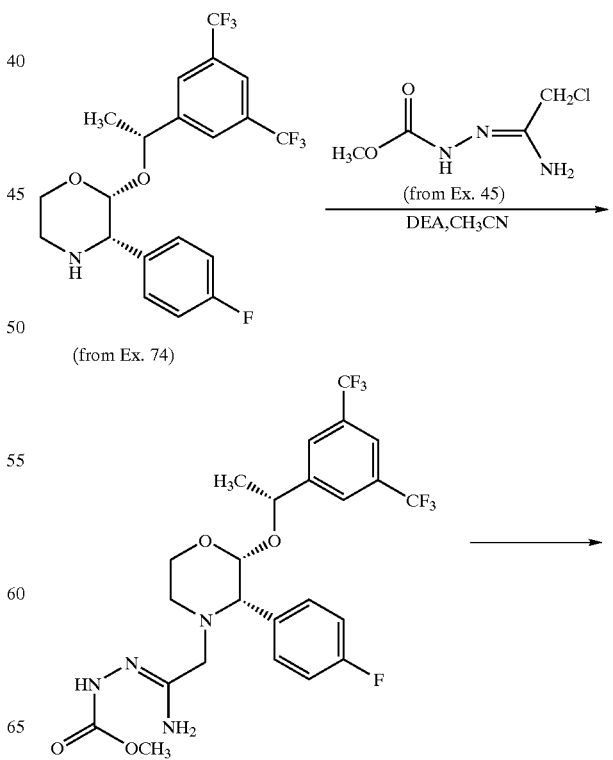

-continued

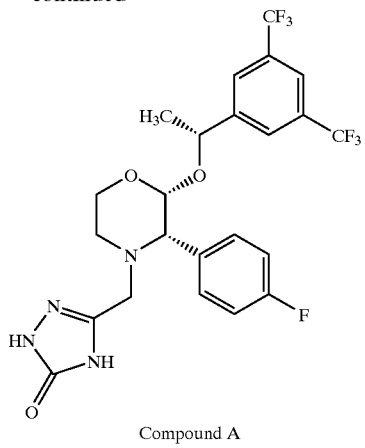

Compound A

More recently, International Patent Publication No. WO 99/65900 (published Dec. 23, 1999) described a convenient, efficient process which utilizes a one-step alkylation with 3-chloromethyl-1,2,4-triazolin-5-one. The synthesis of the chloromethyltriazolinone 1 is described in Examples 2 and 3 of WO 99/65900 which used the base-catalysed cyclisation of an acyl semicarbazide (Scheme 1). Hence, benzyloxyacetyl chloride was condensed with semicarbazide hydrochloride under modified Schotten-Baumann conditions to give crude adduct 2. This was not purified but, instead, was heated in dilute NaOH to induce cyclisation thus giving triazolinone 3 in 60% yield from benzyloxyacetyl chloride. Hydrogenolytic removal of the benzyl protecting group, using ammonium formate as the hydrogen source, gave the water soluble alcohol 4 in excellent yield (98%). Treatment of this compound with thionyl chloride then afforded chloromethyltriazolinone 1 as a stable crystalline solid in 87% yield.

Scheme 1: (a) NaOH, THF/H₂O (5:1), 0°C., 2 h; (b) NaOH (2M aq), reflux, 5 h; (c) Pd on C, HCO₂NH₄, MeOH/H₂O (10:1), 60° C., 4 h; (d) SOCl₂, CH₃CN, 20° C.,18 h.

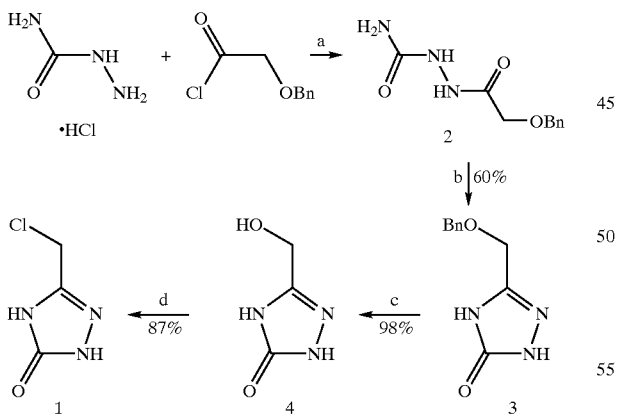

While this synthesis of the chloromethyltriazole 1 allowed the study of the subsequent alkylation reaction to afford Compound A, the cost of the starting acid chloride and the number of steps involved detracted from its viability for large scale synthesis.

There is therefore a need for a simple and efficient synthesis of 3-chloromethyl-1,2,4triazolin-5-one and analogous compounds, that utilizes readily available starting materials.

Thus, in a first aspect of the present invention, there is provided a process for the preparation of a compound of formula (I)

wherein
R represents hydrogen, $C_{1-10}$alkyl, halo$C_{1-10}$alkyl or aryl; which comprises:
(i) reacting a triaryl- or trialkylorthoester of formula (II)

wherein each $R^1$ independently represents $C_{1-10}$alkyl, or aryl, with a semicarbazide of formula (III)

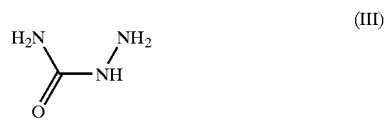

or a salt thereof, in an organic solvent; and
(ii) collecting the resultant compound of formula (I).
In the compounds of formulae (I) and (II), preferably R is hydrogen or, more particularly, a halomethyl group, especially chloromethyl.
In the compounds of formula (II), preferably each $R^1$ is the same. In particular, $R^1$ is preferably a methyl group.
A salt of the compound of formula (III) is preferably used such as a halide, especially the chloride. In other words, the compound of formula (III) is semicarbazide.HCl—i.e.

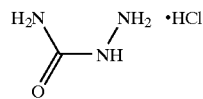

Suitable organic solvents of use in the above reaction include alcohols. Most preferably, the above reaction is effected in methanol.
Conveniently, the above reaction is effected at room temperature.
According to an alternative aspect of the present invention, the compound of formula (I) may be prepared by the reaction of a compound of formula (IV)

or a salt thereof, wherein R and $R^1$ are as previously defined, with. a compound of formula (III) in the presence of an alcoholic solvent.

This reaction proceeds via the in situ formation of an orthoester of formula (II). Thus, in the compound of formula (IV), $R^1$ is preferably a methyl group, and the solvent is preferably methanol.

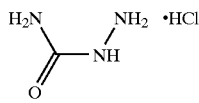

A salt of the compounds of formula (IV) is preferably used such as a halide, especially the chloride. In other words, the compound of formula (III) is semicarbazide.HCl—i.e.

As used herein, the term "$C_{1-10}$alkyl" as a group or part of a group, means a straight or branched alkyl group containing from 1 to 10 atoms. Particularly preferred are $C_{1-6}$alkyl groups including methyl, ethyl, n-propyl, i-propyl, n-butyl, s-butyl and t-butyl. Especially preferred is methyl.

As used herein, the term "halo$C_{1-10}$alkyl" means a straight or branched alkyl group containing from 1 to 10 carbon atoms wherein said alkyl group is substituted by one or more halogen atoms. Suitable halogen atoms include chlorine, bromine or iodine, most especially chlorine. Preferably said alkyl group is substituted by one halogen atom.

As used herein, the term "aryl" means an aromatic radical such as phenyl, biphenyl or naphthyl, wherein said phenyl, biphenyl or naphthyl group may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, NO2, cyano, $SR^a$, $SOR^a$, $SO2R^a$, $COR^a$, $CO_2R^a$, $CONR^a R^b$, $C_{2-6}$alkenyl, $C_{2-6}$alkynyl, $C_{1-4}$alkoxy$C_{1-4}$alkyl or —O(CH$_2$)$_m$ O—, where $R^a$ is hydrogen, $C_{1-4}$alkyl or fluoro$C_{1-4}$alkyl. Preferably said phenyl, biphenyl or naphthyl group is optionally substituted by one or two substituents, especially none or one. Particularly preferred substituents include fluorine, chlorine, bromine, methyl, methoxy, trifluoromethyl and trifluoromethoxy. Most preferably, aryl is a phenyl group.

According to a further aspect of the present invention, there is provided a method for the synthesis of the compounds described in International Patent Publication No. WO 95/16679. In particular, there is provided a method for the synthesis of compounds of formula (A) as described herein. Said method comprises the preparation of a compound of formula (I) according to the method described and claimed herein, followed by one or more synthetic steps to complete the synthesis of the desired compound. Suitable methods for completing the synthesis are described, in particular, in International Patent Publication No. WO 99/65900.

In particular, there is provided the use of a compound of formula (I) when prepared according to the method described and claimed herein in the preparation of the compound 2-(R)(1-(R)-(3,5-bis(trifluoromethyl)-phenyl)ethoxy)-3-(S)-(4-fluorophenyl)4-(3-(5-oxo-1H,4H-1,2,4-triazolo) methyl)morpholine; and pharmaceutically acceptable salts thereof.

According to a yet further aspect of the present invention, there is provided the compound 2-(R)-(1-(R)-(3,5-bis (trifluoromethyl)phenyl)-ethoxy)-3-(S)-(4-fluorophenyl)4-(3-(5-oxo-1H,4H-1,2,4-triazolo)methyl)-morpholine, or a pharmaceutically acceptable salt thereof, prepared by the reaction of a compound of formula (I) with 2-(R)-(1-(R)-(3,5-bis (trifluoromethyl)phenyl)ethoxy)-3-S)-(4-fluorophenyl)morpholine, characterised in that said compound of formula (I) is prepared according to the method described and claimed herein. Suitable methods for completing the synthesis are described, in particular, in International Patent Publication No. WO 99/65900.

The following non-limiting examples illustrate processes according to the present invention:

EXAMPLE 1

3-Chloromethyl-1,2,4triazolin-5-one

A mixture of semicarbzide hydrochloride (5.69 Kg, 51.0 mol), 2-chloro-1,1,1-trimethoxy ethane (94.0 mol) and methanol (54 L) was stirred at room temperature for 4 days. The solvent was then removed under reduced pressure and toluene (25 L) was added. The resulting slurry was cooled to 0° C. and filtered to afford 3-chloromethyl-1,2,4-triazolin-5-one (6.69 Kg, 98%) as a white solid (mp 197–199° C); $^1$H NMR (d$_6$ DMSO) δ=4.43 (2H, s, C$\underline{H}_2$), 11.48 (1H, s, N$\underline{H}$) and 11.64 (1H, s NH); $^{13}$C NMR (d$_6$ DMSO) δ=36.9 (Cl$\underline{C}$ $\underline{H}_2$), 144.6 (CH$_{2\underline{C}}$=N) and 156.9 (NH$\underline{C}$ONH). The difficulty in following the reaction of such water soluble compounds has been overcome using the following HPLC conditions:

| | |
|---|---|
| Column: | Waters Symmetry Shield RP8, 25 cm × 4.6 mm i.d. |
| Column Temperature: | 45° C. |
| Flow Rate | 1.0 mL/min |
| Solvent Programme | 100% A for 15 min then 50% A for 5 min then 100% A for 5 min. |
| Solvent A: | 1 mL of 99.999% phosphoric acid (85 w/w %) is dissolved in 1 litre of water. |
| Solvent B: | Far U.V. HPLC grade acetonitrile is used neat in the solvent reservoir. |
| Retention time: | 7.07 min |

EXAMPLE 2

1,2,4-Triazolin-5-one

A mixture of semicarbazide hydrochloride (10.0 g, 89.6 mmol), trimethyl orthoformate (28.5 g, 269 mmol) and methanol (100 mL) was 15 stirred at room temperature for 2 hours. The reaction was concentrated under reduced pressure and then toluene (100 mL) was added and, after cooling to 0° C., filtration gave the title compound (7.26 g, 100%) as a white solid; $^1$H NMR (d$_6$ DMSO) δ=7.66 (1H, s, C$\underline{H}$, 11.24(1H, s, N$\underline{H}$) and 11.35 (1H, s, N$\underline{H}$; $^{13}$C NMR (d$_6$ DMSO) δ=137.0 (CH$_2$ $\underline{C}$=N) and 156.6 (NH$\underline{C}$ONH).

REFERENCE EXAMPLE A

Preparation of 2-(R)-( 1-(R)-(3.5-bis (trifluoromethyl) phenyl)ethoxy)-3-S)-(4-fluorophenyl)-4-(3-(5-oxo-1H,4H-1,2,4-triazolo) meth l)morpholine A solution of 3-chloromethyl-1,2, 4triazolin-5-one (3.18 g) in DMF (30 ml) was added over 1 hour to a slurry of 2-(R)-(14R)-(3,5-bis (trifluoromethyl)phenyl)ethoxy)-3-(S)-(4-fluorophenyl)morpholine (R)-camphor sulfonic acid salt (15 g) and potassium carbonate (7.71 g) in DMF (100 ml) at 22° C. The reaction mixture was aged at 22° C. for 20 minutes, then water (400 ml) was added over 30 minutes. The crystallising mixture was cooled in an ice bath, aged for 30 minutes and the product collected by filtration. The solid title compound was washed with water (400 ml), air dried and dried in vacuo at 45–50° C. Yield =11.4 g; 98.1% HPLC w/w assay; 93.2% assay yield; (97. 1A% HPLC profile).

REFERENCE EXAMPLE B

Alternative Preparation of 2-(R)-(1-(R)-(3,5-bis (trifluoromethyl)phenyl)-ethoxy)-3-(S)-(4-fluorophenyl)-4-(3-(5-oxo-1H,4H-1,2,4-triazolo) methyl)morpholine (1) B1:- Alternative Method using N,N-diisopropylethylamine DMF A solution of 3-chloromethyl-1,2,4-triazolin-5-one (2.56 g) in DMF (20 ml) was added over 1 hour to a slurry of 2-(R)-(1-(R)43,5-bis(trifluoromethyl)phenyl)ethoxy)-3-(S)-(4fluorophenyl)morpholine para-toluenesulfonic acid salt (12 g) and N,N-diisopropylethylamine (5.15 g) in DMF (40 ml) at 21° C. The reaction was aged at 21–23° C. for 30 minutes, then water (120 ml) was added over 20 minutes. The crystallising mixture was cooled in an ice bath, aged for 30 minutes and the product collected by filtration. The solid title compound was washed with water (96 ml), air dried and dried in vacuo at 50° C. Yield =9.65 g; 99.7% isolated yield.

(2) B2:-Alternative Method using potassium carbonate DMF

A solution of 3-chloromethyl-1,2,4-triazolin-5-one (1.40 g) in DMF (13.5 ml) was added over 1 hour to a slurry of 2-(R)-(1-(R)-(3,5-bis(trifluoromethyl)phenyl)ethoxy)-3-(S)-(4-fluorophenyl)morpholine para-toluenesulfonic acid salt (6.77 g) and potassium carbonate (1.55 g) in DMF (27 ml) at 19° C. The reaction was aged at 19–21° C. for 30 minutes, then water (81 ml) was added over 20 minutes. The crystallising mixture was cooled in an ice bath, aged for 30 minutes and the product collected by filtration. The solid title compound was washed with water (54 ml), air dried and dried in vacuo at 50° C. Yield =5.37 g; 98.0% HPLC w/w assay; 96.4% assay yield.

What is claimed is:

1. A process for the preparation of a compound of formula (I)

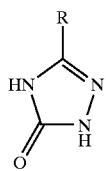

(I)

wherein

R represents hydrogen, $C_{1-10}$ alkyl, halo$C_{1-10}$alkyl or aryl; which comprises:

(i) reacting a triaryl- or trialkylorthoester of formula (II)

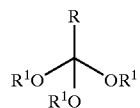

(II)

wherein each $R^1$ independently represents $C_{1-10}$alkyl, or aryl, with a semicarbazide of formula (III)

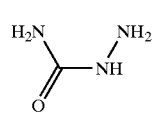

(III)

or a salt thereof, in an organic solvent; and (ii) collecting the resultant compound of formula (I).

2. A process according to claim 1 wherein, in the compounds of formulae (I) and (II), R is hydrogen or a halomethyl group.

3. A process according to claim 2 wherein, in the compounds of formulae (I) and (II), R is a chloromethyl group.

4. A process according to claim 1 wherein, in the compounds of formula (II), each $R^1$ is the same.

5. A process according to claim 4 wherein each $R^1$ is a methyl group.

6. A process according to claim 1 wherein said compound of formula (III) is in the form of a halide salt.

7. A process according to claim 6 wherein said halide salt is the hydrochloride salt.

8. A process according to claim 1 wherein said organic solvent is an alcohol.

9. A process according to claim 8 wherein said alcohol is methanol.

10. A process according to claim 1 wherein said process is effected at room temperature.

* * * * *